United States Patent [19]

Pitchai et al.

[11] Patent Number: 5,208,194
[45] Date of Patent: May 4, 1993

[54] RECOVERY OF GROUP VIII TRANSITION METALS FROM ORGANIC SOLUTIONS USING ACIDIC ION-EXCHANGE RESINS

[75] Inventors: Rangasamy Pitchai; Thomas S. Zak, both of West Chester; Kurt E. Soring, Aston, all of Pa.

[73] Assignee: Arco Chemical Technology, L.P., Wilmington, Del.

[21] Appl. No.: 841,396

[22] Filed: Feb. 25, 1992

[51] Int. Cl.$^5$ .......................... B01J 38/74; B01J 31/40; C01G 55/00; C07C 45/78

[52] U.S. Cl. .......................................... 502/12; 75/426; 423/22; 502/31; 502/32; 502/33; 568/454; 568/492

[58] Field of Search .................. 502/11, 12, 31, 29, 502/33, 24, 22; 423/22; 568/454, 492; 75/426

[56] References Cited

U.S. PATENT DOCUMENTS

| | | | |
|---|---|---|---|
| 2,945,743 | 7/1960 | Zimmerley et al. | 23/24 |
| 3,547,964 | 12/1970 | Olivier | 260/429 |
| 3,560,539 | 2/1971 | Booth | 260/429 |
| 3,567,368 | 3/1971 | Nekvasil et al. | 23/51 |
| 3,755,393 | 8/1973 | Kniese et al. | 260/429 R |
| 3,998,622 | 12/1976 | Balmat | 75/0.5 A |
| 4,007,130 | 2/1977 | Leach et al. | 502/12 |
| 4,069,040 | 1/1978 | Thomas et al. | 75/101 |
| 4,135,911 | 1/1979 | Balmat | 75/0.5 AB |
| 4,292,196 | 7/1981 | Homeier et al. | 252/412 |
| 4,363,765 | 12/1982 | Fiato et al. | 260/429 R |
| 4,388,279 | 6/1983 | Quick | 423/22 |
| 4,396,551 | 8/1983 | Tsunoda et al. | 260/429 R |
| 4,413,118 | 11/1983 | Roberts et al. | 534/7.1 |
| 4,935,550 | 6/1990 | Miller et al. | 568/454 |
| 4,950,629 | 8/1990 | Bodurow | 502/24 |
| 5,085,835 | 2/1992 | Weber et al. | 423/22 |
| 5,091,350 | 2/1992 | Cornils et al. | 502/24 |
| 5,091,546 | 2/1992 | Lappe et al. | 556/23 |
| 5,114,473 | 5/1992 | Abatjoglou et al. | 423/22 |
| 5,124,290 | 6/1992 | Erpenbach et al. | 502/12 |

FOREIGN PATENT DOCUMENTS 0255389  2/1988  European Pat. Off. .

OTHER PUBLICATIONS

J. Am. Oil Chemists Soc. 54 (1977) 276 (DuFek et al.).

Primary Examiner—Paul E. Konopka
Attorney, Agent, or Firm—Jonathan L. Schuchardt

[57] ABSTRACT

A process for recovering a Group VIII metal from an organic solution is disclosed. The organic solution is contacted with an acidic ion exchange resin that has sulfonic acid active groups. The invention provides an effective and economical way to recover valuable transition metals from dilute organic solutions.

16 Claims, No Drawings

RECOVERY OF GROUP VIII TRANSITION METALS FROM ORGANIC SOLUTIONS USING ACIDIC ION-EXCHANGE RESINS

FIELD OF THE INVENTION

The invention relates to recovery of transition metal catalysts. In particular, a process for recovering a Group VIII transition metal compound from an organic solution using an acidic ion-exchange resin is disclosed.

BACKGROUND OF THE INVENTION

Group VIII transition metal compounds are commonly used as homogeneous catalysts for commercially important organic reactions. One such process is hydroformylation, in which an olefin reacts with hydrogen and carbon monoxide in the presence of a Group VIII transition metal compound to give an aldehyde. Hydroformylation of allyl alcohol, for example, gives 4-hydroxybutanal, which is an intermediate in a commercial route to 1,4-butanediol.

A central problem is how best to recover the typically expensive Group VIII transition metal compound from organic mixtures. Conventional approaches to metal recovery include extraction with aqueous solutions, addition of precipitating agents, or a combination of these techniques.

Extraction of Group VIII metals from organic mixtures using aqueous acetic acid (European Patent No. 0 255 389), aqueous amine solutions (U.S. Pat. No. 4,292,196), aqueous alkaline cesium salt solution and crown ether (U.S. Pat. No. 4,363,765), aqueous solutions of ionic organophosphines (U.S. Pat. No. 4,935,550), and amine/HCN mixtures (*J. Am. Oil Chemists Soc.* 54 (1977) 276) have been described.

Precipitation of the Group VIII metal compound, followed by either extraction or filtration of the precipitate is a second general approach. Examples include precipitation by peroxide treatment of an organic mixture containing the Group VIII metal catalyst (U.S. Pat. No. 3,547,964), reductive treatment with hydrogen/catalyst or a hydride reducing agent (U.S. Pat. No. 4,560,539), precipitation of agglomerated rhodium from neutralized distillation residues (U.S. Pat. Nos. 3,998,622 and 4,135,911), oxidation under basic conditions (U.S. Pat. No. 4,396,551), treatment with an organic sulfur compound to form a precipitate (U.S. Pat. No. 4,413,118), and treatment with a carboxylic acid to precipitate an active catalyst (U.S. Pat. No. 4,950,629).

Ion-exchange methods have been used to recover Group VIII metals from aqueous solutions, as described, for example, in U.S. Pat. Nos. 2,945,743 and 3,567,368. U.S. Pat. No. 3,755,393 teaches a method in which a hydroformylation mixture is passed through a basic ion-exchange resin to recover rhodium. U.S. Pat. No. 4,388,279 teaches a process for recovering Group VIII metals from organic solutions using either a solid absorbent such as calcium sulfate, molecular sieves, or an anionic ion-exchange resin. Acidic ion-exchange resins have not been used to recover Group VIII metals from organic solutions.

SUMMARY OF THE INVENTION

The invention is a process for recovering a Group VIII transition metal carbonyl complex from an organic solution. The process comprises contacting the organic solution with an acidic ion-exchange resin that contains sulfonic acid groups, separating the treated solution from the resin, and recovering the metal complex from the resin.

The invention provides an effective and economical way to recover valuable transition metals from dilute organic solutions, and overcomes the need for costly and time-consuming extraction and precipitation techniques.

DETAILED DESCRIPTION OF THE INVENTION

The process of the invention is well-suited for isolation of Group VIII metal catalysts from organic solutions. The Group VIII transition metal carbonyl complexes of the invention are generally homogeneous catalysts, i.e, they are soluble or mostly soluble in the reaction mixture. The complexes can be anionic, neutral, or cationic, but must contain at least one Group VIII transition metal compound and must have at least one carbonyl ligand. Group VIII transition metal hydrido complexes are preferred. Examples of suitable Group VIII transition metal carbonyl complexes include, but are not limited to, $RhH(CO)(PPh_3)_3$, $IrH(CO)(PPh_3)_3$, and the like, and mixtures thereof.

Organic solutions of Group VIII transition metals are used in the invention. Any organic compound that is a solvent for a Group VIII metal carbonyl complex is suitable. Examples of suitable organic solvents include aromatic and aliphatic hydrocrbons, halogenated aromatic and aliphatic hydrocarbons, ethers, and the like, and mixtures thereof. The process of the invention works especially well when the organic solvent is an aromatic hydrocarbon such as benzene or toluene.

Ion-exchange resins useful in the process of the invention are strongly acidic resins that contain sulfonic acid active groups. Preferably, the resin is used in the protonated form, i.e., all of the active groups are —$SO_3H$. Neutralized sulfonic acid resins, in which some or all of the protons have been exchanged by a cation such as an alkali metal are also suitable, although less preferred. Sulfonated copolymers of styrene and divinylbenzene are preferred.

Preferred sulfonic acid resins for use in the process of the invention are macroreticular or macroporous resins having surface areas greater than about 20 $m^2/g$ and porosities greater than about 20%. Particularly preferred are resins having a surface area within the range of about 40 $m^2/g$ and about 100 $m^2/g$, and an average pore radius within the range of about 200 and 300 angstroms. A particularly preferred resin is "Amberlyst 15" resin, a product of Rohm and Haas Company. Strongly basic, weakly basic, neutral, and weakly acidic ion exchange resins are generally unsuitable for use in the process of the invention (see Comparative Examples 5–9).

The process of the invention is especially well-suited for use in a commercially important route to 1,4-butanediol. Propylene oxide is isomerized to give allyl alcohol, which can be hydroformylated to give a mixture of 4-hydroxybutanal and 2-methyl-3-hydroxypropanal. The hydroformylation process is typically performed in a nonpolar organic solvent such as toluene. Extraction of the aldehyde products into water leaves behind a toluene stream that contains a homogeneous rhodium catalyst. Treatment of this stream according to the process of the invention results in excellent recover of the valuable rhodium catalyst in the acidic resin bed. The metal can be easily recovered from the resin by any suitable means. One way to recover the metal is to burn off the resin (an "ashing" process), which leaves the metal behind in a concentrated form suitable for regeneration.

The following examples merely illustrate the invention. Those skilled in the art will recognize numerous variations that are within the spirit of the invention and scope of the claims.

EXAMPLES 1-9

The catalyst solutions used are toluene solutions containing about 100 ppm of rhodium. The solutions are prepared by dissolving RhH(CO)(PPh$_3$)$_3$ in toluene with an excess of triphenylphosphine. The concentration of rhodium [Rh]in each solution is found by elemental analysis. A sample of catalyst solution (100 mL) is mixed intermittently with 5.0 g of dry ion-exchange resin (see Table 1). After about 30 minutes of mixing, the treated solution is separated from the resin and the residual rhodium concentration is determined by elemental analysis. Results of rhodium removal for various ion-exchange resins are recorded in Table 1.

As shown in the table, only sulfonic acid resins are effective for removing most of the rhodium. The most effective resin is "Amberlyst 15" resin, which has a relatively low surface area (45 m$^2$/g) and a relatively large pore radius (255 angstroms). "Amberlyst XN-1010" resin, a sulfonic acid resin that is rather ineffective in removing rhodium, has a higher surface area (540 m$^2$/g) and a smaller pore radius (50 angstroms).

Strongly basic resins (examples C7 and C8), neutral resins (examples C6 and C9), and weakly acidic resins (example C5) are generally ineffective compared with "Amberlyst 15" resin in removing soluble rhodium from toluene solutions.

5. The process of claim 1 wherein the organic solvent is selected from the group consisting of aliphatic and aromatic hydrocarbons.

6. The process of claim 1 wherein the resin has a surface area within the range of about 40 m$^2$/g to about 100 m$^2$/g and an average pore radius within the range of about 200 angstroms to about 300 angstroms.

7. A catalyst-recovery process which comprises:
(a) hydroformylating an organic solution containing allyl alcohol in the presence of a rhodium hydridocarbonyl complex catalyst to produce 4-hydroxybutanal;
(b) extracting 4-hydroxybutanal from the organic solution with water;
(c) recovering the catalyst from the organic solution by contacting the solution with an acidic ion-exchange resin that has sulfonic acid active groups;
(d) separating the resin from the treated solution; and
(e) recovering the rhodium complex from the resin.

8. The process of claim 7 wherein acidic ion-exchange resin is "Amberlyst 15" resin.

9. The process of claim 7 wherein the rhodium hydridocarbonyl complex is HRh(CO)(PPh$_3$)$_3$.

10. The process of claim 7 wherein the rhodium complex is recovered from the resin by an ashing process.

11. The process of claim 7 wherein the organic solvent is selected from the group consisting of aliphatic and aromatic hydrocarbons.

12. The process of claim 7 wherein the resin has a surface area within the range of about 40 m$^2$/g to about 100 m$^2$/g and an average pore radius within the range of about 200 angstroms to about 300 angstroms.

13. A rhodium-recovery process which comprises contacting a solution of HRh(CO)(PPh$_3$)$_3$ catalyst in an organic solvent selected from the group consisting of

TABLE 1

Rhodium Recovery from Hydroformulation Stream using Sulfonic Acid Ion-Exchange Resin

| Ex # | Resin | Active groups | [Rh] before treatment, ppm | [Rh] after treatment, ppm | Rhodium removed, % |
|---|---|---|---|---|---|
| 1 | Amberlyst 15[a] | —SO$_3$H | 92 | 1.2 | 99 |
| 2 | Amberlyst 15, neutralized[b] | —SO$_3$$^-$Na$^+$ | 99 | 13 | 87 |
| 3 | Amberlyst 18[c] | —SO$_3$H | 110 | 34 | 69 |
| 4 | Amberlyst XN-1010[d] | —SO$_3$H | 95 | 77 | 19 |
| C5 | Amberlite IRC-50 | —COOH | 110 | 110 | 0 |
| C6 | Amberlite IRC-718 | —COO$^-$Na$^+$ | 110 | 110 | 0 |
| C7 | Amberlite IRA-400(OH) | —NR$_3$$^+$$^-$OH | 110 | 110 | 0 |
| C8 | Amberlyst A26 | —N(CH$_3$)$_3$$^+$Cl$^-$ | 99 | 77 | 22 |
| C9 | Phosphinated S/DVB | —PPh$_2$ | 120 | 80 | 33 |

All resins were rinsed with water, then ethanol, then toluene, and were oven-dried at 120° C.
Phosphinated S/DVB = phosphinated styrene-divinylbenzene copolymer
[a]surface area = 45 m$^2$/g, pore radius = 255 angstroms
[b]prepared by rinsing Amberlyst 15 resin with aqueous NaCl, then water, ethanol, etc.
[c]pore radius = 480 angstroms
[d]surface area = 540 m$^2$/g, pore radius = 50 angstroms
All "Amberlyst" and "Amberlite" resins (Examples 1-8) are products of Rohm and Haas Company

We claim:

1. A rhodium-recovery process which comprises contacting a solution of a rhodium hydridocarbonyl complex in an organic solvent with an acidic ion-exchange resin that has sulfonic acid active groups, separating the resin from the treated solution, and recovering the rhodium complex from the resin.

2. The process of claim 1 wherein acidic ion-exchange resin is "Amberlyst 15" resin.

3. The process of claim 1 wherein the rhodium hydricarbonyl complex is HRh(CO)(PPh$_3$)$_3$.

4. The process of claim 1 wherein the rhodium complex is recovered from the resin by an ashing process.

aromatic and aliphatic hydrocrbons, halogenated aromatic and aliphatic hydrocarbons, ethers, and mixtures thereof, with an acidic ion-exchange resin that has sulfonic acid active groups, a surface area within the range of about 40 m$^2$/g to about 100 m$^2$g and an average pore radius within the range of about 200 angstroms to about 300 angstroms, separating the resin from the treated solution, and recovering the catalyst from the resin.

14. The process of claim 18 wherein the acidic ion-exchange resin is "Amberlyst 15" resin.

15. The process of claim 13 wherein the catalyst is recovered from the resin by an ashing process.

16. The process of claim 13 wherein the organic solvent is an aromatic hydrocarbon.

* * * * *